United States Patent [19]

Raleigh et al.

[11] Patent Number: 5,008,103
[45] Date of Patent: Apr. 16, 1991

[54] SILICONE SURFACTANTS

[75] Inventors: William J. Raleigh, Rensselaer; Raymond J. Thimineur, Scotia; Anthony A. Zotto, Troy, all of N.Y.

[73] Assignee: General Electric Company, Waterford, N.Y.

[21] Appl. No.: 291,909

[22] Filed: Dec. 29, 1988

[51] Int. Cl.$^5$ .......................... A61K 7/32; A61K 7/34; A61K 7/38
[52] U.S. Cl. ................. 424/66; 424/DIG. 5; 424/47; 424/68; 424/69; 514/938
[58] Field of Search ...................... 424/66, 68

[56] References Cited

U.S. PATENT DOCUMENTS

| | | | |
|---|---|---|---|
| 2,846,458 | 8/1958 | Haluska | 260/448.2 |
| 3,234,252 | 2/1966 | Pater | 260/448.2 |
| 3,427,271 | 2/1969 | McKellar | 260/29.2 |
| 3,657,305 | 4/1972 | Morehouse | 260/448.2 |
| 4,047,958 | 9/1977 | Yoneyama et al. | 96/87 |
| 4,122,029 | 10/1978 | Gee et al. | 252/309 |
| 4,218,250 | 8/1980 | Kasprzak | 106/3 |
| 4,265,878 | 5/1981 | Keil | 424/68 |
| 4,268,499 | 5/1981 | Keil | 424/68 |
| 4,311,695 | 1/1982 | Starch | 424/184 |
| 4,499,069 | 12/1985 | Krafton | 424/66 |
| 4,526,780 | 7/1985 | Marschner et al. | 424/66 |
| 4,552,753 | 11/1985 | Elm et al. | 424/66 |
| 4,782,095 | 11/1988 | Gunn | 514/937 |
| 4,822,603 | 4/1989 | Farris | 424/66 |

OTHER PUBLICATIONS

Chemical Abstracts, 1977, vol. 87, (2), p. 11468f.
Chemical Abstracts, 1987, vol. 108, p. 62269b.

Primary Examiner—Dale R. Ore
Attorney, Agent, or Firm—John L. Young

[57] ABSTRACT

Novel polysiloxane polymers are provided having general formula

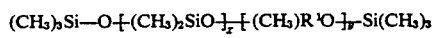

wherein $R^1$ is a polyoxyalkylene radical of the formula

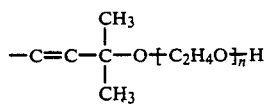

x has an average value from about 5 to 400, y has an average value of at least 1 and n has an average value from at least 1 to 200. Water-in-oil emulsions comprising the novel polysiloxane polymers are also described.

1 Claim, No Drawings

SILICONE SURFACTANTS

The present invention relates to novel polysiloxane-polyether copolymers and their use in stabilizing water-in-oil emulsions, such as polishes and antiperspirant compositions of the so-called dry-feeling type, comprising an emulsion of water in a volatile, water-insoluble liquid.

BACKGROUND OF THE INVENTION

A variety of polysiloxane-polyether or polysiloxane-polyoxyalkylene copolymers is known to the art, and the copolymers have found many uses including the manufacture of polyurethane foams and emulsification of one of a pair of immiscible liquids in the other, such as water-in-oil, oil-in-water and oil-in-oil emulsions.

The use of polysiloxane surface active agents comprising organic polyether groups to stabilize emulsions is well known. U.S. Pat. No. 4,265,878 uses a polysiloxane surface active agent to stabilize antiperspirant stick compositions. U.S. Pat. No. 4,218,250 uses such a polysiloxane surface active agent to stabilize polish formulations. U.S. Pat. No. 4,268,499 uses such surface active agents to stabilize antiperspirant emulsion compositions. Further, U.S. Pat. No. 4,311,695 uses such surface active agents in personal care creams and the like.

Polysiloxane surface active agents are sometimes referred to as polysiloxane-polyoxyalkylene copolymers. However, their use to date as stabilizers for silicone emulsions, particularly water-in-oil emulsions, has not always been completely satisfactory because the variables affecting their function are not well understood. Water-in-oil emulsions which contain high concentrations of salts or other ionic materials are often particularly difficult to stabilize. The problems encountered in formulating emulsions of antiperspirants in volatile fluids are exemplary of this.

Antiperspirant compositions are well known in the cosmetic art. These compositions are formulated as aerosols, gels, sticks, creams, pump sprays and lotions and comprise an astringent, typically comprising one or more zirconium salts and/or aluminum salts, in various forms such as a dry, impalpable powder, an alcohol solution or an aqueous solution. Of these various forms of astringents the aqueous solution is generally considered to be the most effective antiperspirant.

An antiperspirant composition having water as the continuous phase, such as an aqueous solution of an astringent, or an oil-in-water type emulsion thereof, is less desirable because it tends to feel wet when applied to the human skin and to go through a tacky state during the drying period after application. Therefore the use of water-in-oil emulsions to apply antiperspirants to the skin has found favor.

U.S. Pat. No. 4,122,029 discloses water-in-oil type compositions having broad utility and comprising a polydiorganosiloxane-polyoxyalkylene copolymer and a water-in-oil type surfactant. When formulated as an antiperspirant emulsion of an aqueous solution of an astringent such as aluminum chlorhydrate emulsified in a volatile, non-aqueous continuous phase, these compositions have a desirable dry feeling when applied to the human skin.

U.S. Pat. No. 4,268,499 discloses compositions described as having greater efficacy than those of U.S. Pat. No. 4,122,029. The efficacy was determined by applying compositions to subjects' wrists and measuring the time required for the compositions to begin to dry and turn white.

Another type of water-in-oil emulsion which has found favor with the public is polishes, particularly for furniture. One drawback to furniture polishes which utilize organic or organosilicon surfactants comprising long chain oxyalkylene residues, particularly long chain oxyethylene residues, is that the surfactant may tend to attack the finish of the article to be polished. This is particularly the case when the finish is based on nitrocellulose lacquers since glycol ethers are solvents of choice for nitrocellulose finishes.

SUMMARY OF THE INVENTION

It is an object of the present invention to produce novel polysiloxanes containing organic polyether groups.

It is another object of the invention to provide stable emulsions of polar liquids in non-polar liquids.

It is another object of this invention to provide stable emulsions of polar liquids in low-viscosity polydimethylsiloxanes.

It is another object of this invention to provide stable emulsions of aqueous solutions in low-viscosity polydimethylsiloxanes.

It is another object of the present invention to produce polysiloxane surface active agents for use in formulating polishes, sun screen oils, antiperspirant sticks and lotions, body lotions and the like.

These and other objects are realized by the compositions of this invention wherein a polar liquid is dispersed in a non-polar base liquid by the action of a mixture comprising certain novel polydiorganosiloxane-polyoxyalkylene copolymers.

The polar liquid, which is insoluble in the non-polar base liquid, is the dispersed phase and the base liquid is the continuous phase in the compositions of the invention.

Compositions of this invention wherein the polar liquid comprises water, such as aqueous solutions of personal care products such as insect repellents and anti-perspirants and the base liquid comprises a polydimethylsiloxane, such as cyclopolydimethylsiloxanes, are of particular interest because of the aesthetic value of the feel of said composition when applied to the human skin.

DETAILED DESCRIPTION OF THE INVENTION

The novel polysiloxane polymers of the invention comprise polymers of the general formula (I):

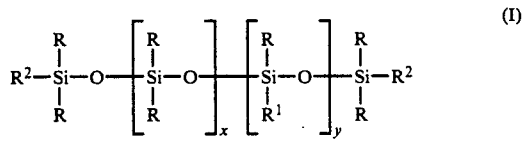

wherein each R individually is an alkyl radical having from 1 to 4 carbon atoms;
$R^I$ is a polyoxyalkylene radical of the formula (II)

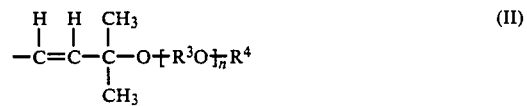

wherein each $R^3$ individually is an alkylene radical having from 2 to 6 carbon atoms, $R^4$ is chosen from the group consisting of R, acyl groups having at least 2 carbon atoms, and hydrogen, and n has an average value of from at least 1 to about 200;

each $R^2$ individually is chosen from the group consisting of R and $R^1$;

x has an average value of from about 5 to about 400; and y has an average value of at least 1 except that when $R^2$ is $R^1$, y may be zero.

The groups represented by R in formula (I) include alkyl radicals such as methyl, ethyl, butyl and the like. It is preferred that at least 80 mole percent of the R groups be methyl.

In the polyoxyalkylene radicals $R^1$ represented by formula (II), the oxyalkylene groups represented by $R^3O$ suitably include —$CH_2CH_2O$— (oxyethylene), —$CH_2CH(CH_3)O$— (oxypropylene), —$CH_2C(CH_3)_2O$—, —$(CH_2)_5O$— and the like. For many applications it is preferred that at least 50% by number of $R^3O$ radicals be oxyethylene. In applications where the surface active agents of the invention are to be utilized to prepare water-in-oil emulsions it is preferred that all of the $R^3O$ radicals be oxyethylene. The balance between oxyethylene and higher oxyalkylene groups such as oxypropylene in the polyether radical (II) may be utilized to alter the degree of hydrophilicity of the surfactant of the invention. When the polyether is all oxyethylene groups, maximum hydrophilicity is achieved. As more of the hydrophobic higher oxyalkylene groups are introduced, the hydrophilic nature of the polyether decreases and thus that of the polysiloxane polyoxyalkylene copolymer surfactant.

In formula (II), $R^4$ is the terminal group of the polyoxyalkylene radical $R^1$. The nature of $R^4$ is not critical and $R^4$ may be chosen from R groups such as methyl, ethyl and the like, acyl groups such as acetyl, and hydrogen. However, when the polysiloxane-polyoxyalkylene copolymer is used to stabilize water-in-oil emulsions, it is preferred that $R^4$ be hydrogen.

The average value of n, the length of the oxyalkylene chains in formula (II), is not critical and may vary broadly from at least 1 to 200 or more. The value of n selected for a particular application will be determined largely by the surfactant properties desired in the product as discussed below. It should be recognized that as the length of the oxyalkylene chains increases, the viscosity of the polyether-polysiloxane will increase, and it may be convenient or even necessary to dilute the surfactant with relatively inert solvents when n is very large.

The average value of x in formula (I) also is not critical and may be varied from about 5 to 400 or more. It should be recognized that as x increases the viscosity of the polyether-polysiloxane will increase, and at higher values of x it may be convenient or even necessary to dilute the surfactant with relatively inert solvents such as hydrocarbon solvents, cyclic polysiloxanes such as octamethyl-cyclotetrasiloxane, polyoxyalkylene ethers and the like as are well-known to the art.

The average value of y in formula (I) likewise is not critical but must be at least 1 except that when $R^2$ is $R^1$, y may be zero. The utility of unsubstituted polysiloxane polymers as "anti-surfactants" in breaking emulsions is well known. When $R^2$ is R, as the average value of y is reduced toward 1, it is statistically possible that in some polymer molecules y will be zero. These homopolymer molecules may interfere with the surfactant activity of the bulk polymer and reduce the effectiveness of the surfactants for some applications. Therefore, when $R^2$ is R it may be advisable to design or formulate the surfactants for such uses in a manner that will lead to an average value of y somewhat greater than 1.

The surfactant properties of individual polyether-polysiloxanes of the invention of the general formula (I) are governed by the balance chosen between the number of hydrophobic diorganosiloxy groups (the value of x), the number of relatively hydrophilic polyoxyalkylene chains $R^1$ (the value of y), the nature of the oxyalkylene groups $R^3O$ in the radical represented by $R^1$, and the average number of oxyalkylene groups n in each chain. For example, a polyether-polysiloxane of the invention may be made more hydrophilic by increasing the value of y with respect to x, thereby increasing the concentration of hydrophilic polyoxyalkylene groups with respect to diorganosiloxy groups, by increasing the concentration of relatively hydrophilic oxyethylene groups with respect to higher oxyalkylene groups in $R^1$, or increasing the number of oxyalkylene groups in the chain (the value of n), or combinations thereof. To decrease the hydrophilicity of a surfactant, the reverse of the above principles would be applied. Those skilled in the art of polyether-polysiloxane surfactants are able to develop polymers suitable for particular applications by utilizing the above criteria without undue experimentation.

The polyether-polysiloxane copolymers (I) of the invention are prepared by reaction of polyoxyalkylene ethers of the general formula (III)

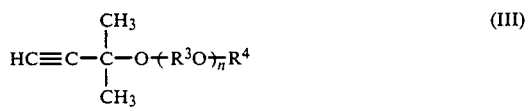

(III)

where n, $R^3$ and $R^4$ are as in general formula (II) above, with hydrogen-containing polysiloxanes corresponding to the general formula (I) but where all $R^1$ groups are hydrogen, using a platinum catalyst such as chloroplatinic acid as is well known in the art. The disclosures of U.S. Pat. Nos. 3,657,305; 3,234,252; 4,047,958; 3,427,271 and 2,846,458 further describe methods for reacting unsaturated polyethers with hydrogen-containing polysiloxanes to prepare polyether-polysiloxane copolymers.

It must be understood that the silicon-bonded hydrogen groups are intended to be completely reacted in the preparation of the copolymers of the invention, but trace amounts may escape reaction and be identifiable in the polyether-polysiloxane polymers of the invention. The preferred method is to use the unsaturated polyether in more than stoichiometric amounts to ensure complete reaction of the silicon-bonded hydrogen. This in turn means that the product of the invention may contain some unreacted polyoxyalkylene ether.

The polyoxyalkylene ethers of general formula (III) above may be prepared by initiating the polymerization of one or more alkylene oxides using the acetylenic alcohol 3-methylbut-1-yn-3-ol (IV) as a starter

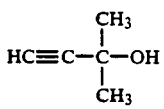

$$\text{HC} \equiv \text{C} - \underset{\underset{\text{CH}_3}{|}}{\overset{\overset{\text{CH}_3}{|}}{\text{C}}} - \text{OH} \qquad (IV)$$

using acidic or basic catalysts as is well known to the art. On completion of the polymerization reaction, the polyether product will correspond to the general formula (III) where $R^4$ is hydrogen. In general, if other endgroups $R^4$ are desired, they are introduced by the known methods for etherification (when $R^4$ is alkyl) or esterification (when $R^4$ is acyl).

The water-in-oil emulsions of the invention comprise;
(a) a polar liquid, optionally containing dissolved inorganic salt(s) as a discontinuous phase;
(b) a volatile liquid having a normal boiling point less than 250° C. as a continuous phase, said volatile liquid being selected from the group consisting of methylsiloxane fluids having the average unit formula

$(CH_3)_a SiO_{(4-a)/2}$ wherein a has an average value of from 2 to 3 inclusive and paraffinic hydrocarbon fluids;
(c) a polydiorganosiloxane-polyoxyalkylene copolymer of the general formula (I) described above; and optionally,
(d) an organic oil-in-water type surfactant having an HLB value of from 8 to 18 inclusive.

Polar liquid (a) of the compositions of this invention is the dispersed phase therein and may comprise one or more efficacious components such as an anti-perspirant, a humectant, an insect repellent, an odorant, a deodorant, an emollient, an antiseptic, a sunscreen agent, a cleansing agent, a suitable pharmaceutical, or the like.

The polar liquid (a) may be any suitable liquid composition which is insoluble at room temperature in the base oil, hereinafter described. By polar it is meant a substance which has a permanent dipole moment. Of course, to maintain the identity of the compositions of this invention the polar liquid should not undergo chemical reaction with remaining components of the composition. The polar liquid may be a pure liquid or a liquid solution or a mixture of immiscible liquids, the components of which are polar and insoluble in the base oil. Solid polar materials may be used as component (a) if they are changed to a liquid form such as by heating to melt the solid or by dissolving the solid in a solvent.

Examples of suitable materials which are polar include inorganic materials such as water, salts, weak acids, weak bases, and aqueous solutions thereof, and organic materials bearing polar groups such as organic compounds bearing nitrogen-containing groups such as in amides, amines, amine salts, nitriles, imides, imines, lactams, and nitro compounds; oxygen-containing groups such as in ethers, alcohols, and in carbonyl groups such as in ketones, aldehydes, carboxylic acids and their salts, esters and lactones; phosphorus-containing groups such as in phosphates and phosphonium salts; sulfur-containing groups such as in sulfones, mercaptans, sulfoxides and sulfides; and halogens such as in hydrocarbon chlorides, bromides, and iodides. The presence of said polar groups in the organic material provides a permanent dipole moment and thus provides the polar character in the organic material.

Emulsion compositions of this invention wherein the polar liquid comprises water and/or ethanol are particularly useful. In common with oil-in-water emulsions, water-in-oil emulsions are desirable from an economic safety and environmental viewpoint as a means of preparing, storing, shipping, and using effacacious components. In addition, emulsion compositions of aqueous or ethanolic solutions in methylsiloxane fluids have value as personal care compositions, as noted above.

Polar liquids (a) of particular interest for the compositions of this invention are therefore selected from the group consisting of water, water solutions of polar solutes, polar liquids soluble in water, ethanol, ethanol solutions of polar solutes and polar liquids soluble in ethanol. Suitable water solutions comprise, as the polar solute, inorganic solutes hereinbefore exemplified and organic solutes such as alcohols such as methanol, ethanol, phenol, ethylene glycol, propylene glycol, glycerine, and their partial ethers and partial esters; nitrogen compounds such as amides such as formamide, acetamide, N-methylacetamide, N,N-dimethyl formamide and urea, nitriles such as acetonitrile and amines and their salts, acids such as formic acid, acetic acid, benzoic acid, stearic acid, and ethylenediaminetetracetic acid and ethers such as furan, tetrahydrofuran, dioxane, ethylene glycol dimethyl ether, propylene glycol dimethylether and their polymeric forms such as triethylene glycol diethyl ether. Suitable ethanol solutions comprise any suitable ethanol-soluble inorganic or organic solute exemplified above as the solute as well as other polar solutes which are insoluble in water but soluble in ethanol such as 2-ethyl-1,3-hexanediol, N,N-diethyltoluamide and 2-ethylhexyl-p-dimethylaminobenzoate.

The base oil or volatile liquid (b) is a fluid selected from the methylsiloxane fluids having a normal, i.e. atmospheric pressure, boiling point of less than 250° C., a paraffinic hydrocarbon, or their mixtures. The volatile methylsiloxane fluid (b) has the average unit formula

$(CH_3)_a SiO_{(4-a)/2}$ where a has an average value of from 2 to 3 and consists of siloxane units selected from the group consisting of $(CH_3)_3SiO_{1/2}$ $(CH_3)SiO_{2/2}$, $CH_3SiO_{3/2}$ and $SiO_{4/2}$ units. Preferably, the volatile methylsiloxane fluid consists essentially of dimethylsiloxane units, and optionally, trimethylsiloxane units. Of particular value as volatile liquid (b) are the cyclic siloxanes of the general formula $[(CH_3)_2SiO]_b$ and the linear siloxanes of the general formula $(CH_3)_3SiO[(CH_3)_2SiO]_cSi(CH_3)_3$, and their mixtures, wherein b is an integer of from 3 to 6 and c is an integer of from 0 to 4. A highly preferred methylsiloxane fluid is a mixture of said cyclic siloxanes wherein a major portion is tetramer (b=4).

Paraffinic hydrocarbon fluids suitable for use in these compositions correspond to the average unit formula $C_nH_{2n+2}$, wherein n is an integer having a value such that the paraffinic hydrocarbon is fluid at room temperature. Of particular value as a base liquid in volatile compositions are the paraffins having a value of n less than 15 such as kerosene, gasoline, and the gaseous paraffins. Of course, gaseous paraffins, in order to be operative in the dispersions of this invention, must be used at low temperature and/or super-atmospheric pressure to keep them in the liquid state.

The base oil, in addition to being a methylsiloxane fluid or a paraffin, may be any mixture of said methylsiloxane fluid and said paraffin such as a mixture of octamethylcyclotetrasiloxane and hexane or decamethylcyclopentasiloxane and butane or a mixture of two or more of said cyclosiloxanes and one or more paraffins.

Component (c) is a polydiorganosiloxane-polyoxyalkylene copolymer preferably containing polydimethylsiloxy groups, and on average at least one polyoxyalkylene group, having the general formula (I) described above.

Component (d) is any cationic, anionic or nonionic organic surfactant suitable for preparing emulsions of the oil-in-water type and having an HLB value of from 8 to 18, inclusive. Examples of oil-in-water type surfactants include polyethoxylated quaternary ammonium salts and polyoxyethylene fatty amines as cationic surfactants, and polyethylene-glycol alkylethers, polyethyleneglycol alkylarylethers, polyethoxylated sorbitan monolaurate, polyethoxylated sorbitan monooleate, polyoxyethylene lanolin derivatives, and polyethoxylated fatty alcohols as nonionic surfactants. Mixtures of cationic and/or nonionic oil-in-water surfactants are also suitable. Other examples of suitable organic surfactants having an HLB value of from 8 to 18 may be found by consulting standard publications such as McCutcheon's "Detergents and Emulsifiers" 1975 North America Edition, MC Publishing Co., Glen Rock, N.J. 1975.

The amounts of components (a) and (b) that may be present in the compositions of this invention may vary widely and comprise, in total, from 99.5 to 91 percent by weight of the total weight of components (a) through (d). The polar liquid (a) may comprise from 89.5 to 50, preferably 85 to 60, weight percent of components (a) through (d); the volatile liquid (b) comprises from 10 to 45, preferably 15 to 35 weight percent of the total weight of components (a) to (d).

The surfactant mixture, consisting essentially of component (c) and optionally (d) comprises, in total, from 0.5 to 9 percent by weight of the total weight of components (a) and (d), with component (c) accounting for from 0.5 to 6 weight percent of the total of components (a) to (d).

The compositions of this invention may further comprise additional components useful in consumer products which are insoluble in the polar phase. Examples of such components include waxes; colorants; perfumes; viscosity control additives, such as solvents or thickening agents for the continuous phase; and non-volatile organopolysiloxanes, such as polydimethylsiloxanes having a viscosity of from 5 to 10,000 centipoise at 25° C.

The compositions of this invention may be prepared by mixing the proper portions of the individual components in any order. Although the compositions of the invention are delineated in terms of a polar liquid (a) emulsified in a volatile liquid, (b), using a mixture of surfactants, (c) and (d), the following examples employ the preferred method of preparing a so-called polar or aqueous phase (a) and any oil-in-water type surfactant (d) and preparing a so-called oil phase comprising the volatile liquid (b) and the polydiorganosiloxane-polyoxyalkylene copolymer (c) and thereafter mixing the so-called aqueous phase with the so-called oily phase. If any component is a solid, it is converted to a liquid form by melting or dissolving before the emulsion is formed. Mixing may be done using standard emulsifying methods.

In order that those skilled in the art may better understand how the present invention can be practiced, the following specific components and examples are disclosed for purposes of illustrating and not limiting the invention. All percentages and parts are by weight, and all viscosities were measured in centipoise at 25° C.

EXPERIMENTAL

Examples 1-8

The copolymers of Examples 1-8 were prepared from trimethylsiloxy endblocked polysiloxanes containing methylhydrogensiloxy units of the general formula

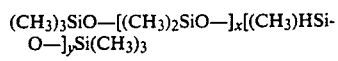

having values of "x" and "y" as shown in Table I. These polysiloxanes are readily prepared by equilibration of appropriate (stoichiometric) amounts of hexamethyldisiloxane, a cyclic telomer of dimethylsiloxy groups and a telomer of methylhydrogensiloxy groups as is well known in the art.

The polysiloxane-polyether copolymers were prepared in the following manner. A known amount of starting polysiloxane containing methylhydrogensiloxy groups was charged to a reactor with an equal amount of toluene. The mixture was refluxed to remove toluene-water azeotrope, decanting and recycling the toluene to the reactor until the mixture was dry. The system was cooled to 100° C and a small amount (about 1% on reactants) of a 0.2N solution of sodium acetate in methanol/isopropanol was added, followed by approximately 0.04% on reactants of a solution of chloroplatinic acid in octanol containing 3.5% platinum. Over a period of about an hour 2-(3-methyl-3-butynoxy)ethanol, "MBEO 1.8 Adduct", manufactured by Air Products and Chemicals, Inc., Allentown, Pa., corresponding to the polyether group desired in the product in a quantity equal to 110% of the stoichiometric amount was fed to the reactor with stirring. The mixture was held at 100° C. with stirring for an additional 4 hours. The toluene was then stripped under vacuum with heating until the temperature of the mixture reached 130° C. at 10 mm Hg pressure. The product was then cooled, filtered, and stored until used.

TABLE I

| | "x" | "y" | % Silicone | % Polyether |
|---|---|---|---|---|
| Example 1 | 15 | 1 | 78 | 22 |
| Example 2 | 100 | 18 | 73 | 27 |
| Example 3 | 200 | 35 | 73 | 27 |
| Example 4 | 100 | 30 | 64 | 36 |
| Example 5 | 100 | 3 | 94 | 6 |
| Example 6 | 10 | 1 | 84 | 16 |
| Example 7 | 20 | 6 | 65 | 35 |
| Example 8* | 0 | 20 | 27 | 73 |

*Product gelled, probably because side reactions between terminal hydroxyl and silanic hydrogen caused significant cross-linking.

EXAMPLE 9

The surfactants of Examples 1-3 were each formulated into the antiperspirant emulsions shown in Table II.

TABLE II

| | Formulation | |
|---|---|---|
| Ingredient | A | B |
|---|---|---|
| Octamethylcyclotetrasiloxane | 15.0 | 20.0 |
| Surfactant (10% in octamethyl-cyclotetrasiloxane) | 16.5 | 11.0 |
| Polysorbate 80 | 0.2 | 0.13 |
| Aluminum zirconium chlorohydrate glycine complex (Wickenol 369) | 20.0 | 20.0 |

TABLE II-continued

| Ingredient | Formulation A | Formulation B |
|---|---|---|
| Water | 48.3 | 48.87 |

In each instance the surfactant was combined with octamethylcyclotetrasiloxane to form an oil phase. Wickenol 369, Polysorbate 80 and water were combined in the aqueous phase. The aqueous phase was added to the oil phase with good mixing until a homogeneous emulsion formed. Then this mixture was homogenized on a Polytron at 13,000 RPM for 30 seconds. The batch size in each case was between 400–500 grams.

The emulsions were examined for stability at room temperature and at 50° C. The emulsions prepared with the surfactant of Example 1 had marginal stability, perhaps because when the average value of "y" is one, the surfactant contains a significant concentration of polydimethylsiloxane, which may destabilize the emulsion. The emulsions prepared with the surfactants of Examples 2 and 3 were stable at both temperatures.

EXAMPLE 10

A water-in-oil emulsion useful as a furniture polish was prepared in the following fashion using the product of Example 7 as the emulsifier.

| Material | Parts by Weight | |
|---|---|---|
| Part A | | |
| Water | | 59.6 |
| Wax emulsion containing | | 3.5 |
| Oxidized microcrystalline wax | 20.0 | |
| Oleic acid | 3.0 | |
| Morpholine | 4.0 | |
| Water | 73.0 | |
| | 100.0 | |
| Part B | | |
| Mineral spirits (1) | | 32.5 |
| Polydimethylsiloxane oil (500 cps) | | 1.7 |
| Polydimethylsiloxane oil (1000 cps) | | 1.7 |
| Product of Example 7 | | 1.0 |
| | | 100.0 |

(1) Use of a deodorized hydrocarbon such as Isopar C or E would be preferred.

First the components of Part A and Part B were each blended separately, and then Part A was added to Part B with high speed agitation.

In typical fashion the resulting polish separated slightly on prolonged standing but redispersed easily with gentle shaking. When applied to a surface, the emulsion broke quickly on rubbing the surface with a soft cloth and imparted an esthetically pleasing polished appearance to the surface. Perhaps because the polyether side chain is hydroxyl-terminated and/or because the ether side chain is short, the polish shows a reduced tendency to attack a nitrocellulose-based finish.

EXAMPLE 11

A stick antiperspirant composition was prepared using the product of Example 4 as the emulsifier.

| Material | Parts by Weight |
|---|---|
| Part A | |
| Octamethylcyclotetrasiloxane | 24.00 |
| Product of Example 7 | 1.00 |
| Stearyl alcohol | 11.25 |
| Methyl Hydroxy Stearate (Paricin 1) | 3.75 |
| Talc | 7.50 |
| Polysorbate 81 (Tween 81) | 0.10 |
| Part B | |
| Aluminum-zirconium tetrachlorohydrate glycine salt (Wickenol 369) | 25.00 |
| Water | 27.40 |
| | 100.00 |

The components of Part A were mixed together and warmed to 60° C. until all the wax melted, using mild stirring to ensure a homogeneous mixture. The components of Part B were also warmed to 60° C. and added to Part A with moderate agitation. When the emulsion became homogeneous, it was cooled to 52° C. while continuing mixing. The preparation was then poured into suitable containers and allowed to cool to ambient temperature. The resulting antiperspirant stick was uniform in appearance and had good consistency, but additional formulation work would be required to optimize the strength of the stick.

EXAMPLE 12

A water-in-oil emulsion cosmetic composition such as is used for a body or night cream was prepared using the product of Example 4 as the emulsifier.

| Material | Parts by Weight |
|---|---|
| Part A | |
| Mineral oil | 15.0 |
| Mixture of Mineral Oil, Petrolatum, Ozokerite, Glyceryl Oleate and Lanolin Alcohol (Protegin X) | 5.0 |
| Product of Example 4 | 2.0 |
| Part B | |
| Polysorbate 80 | 0.4 |
| Sodium Chloride | 2.0 |
| Water | 75.6 |
| | 100.00 |

The elements of Parts A and B were separately mixed. Then Part B was added to Part A with high speed mixing. The resulting emulsion has a smooth creamy composition which was easily spread on the skin. Care to avoid overmixing must be taken, as overmixing tends to cause the emulsion to invert to an oil-in-water system.

What is claimed is:

1. An antiperspirant emulsion composition comprising (a) polar liquid, containing an aqueous solution of an antiperspirant salt as a discontinuous phase;
   (b) a volatile liquid having a normal boiling point less than 250° C. as a continuous phase, said volatile liquid being selected from the group consisting of methylsiloxane fluids having the average unit formula $(CH_3)_a SiO_{(4-a)/2}$ wherein a has an average value of from 2 to 3 inclusive and paraffinic hydrocarbon fluids;
   (c) a polysiloxane surface active agent comprising polymers of the formula (I):

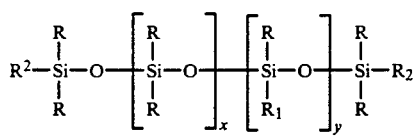
(I)

wherein each R individually is chosen from the group consisting of alkyl having from 1 to 4 carbon atoms; $R^1$ is a polyoxyalkylene radical of the formula

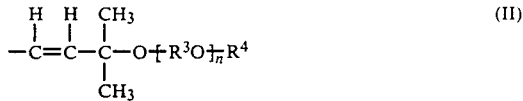
(II)

wherein each $R^3$ individually is an alkylene having from 2 to 6 carbon atoms, $R^4$ is chosen from the group consisting of R, acyl groups having at least 2 carbon atoms, and hydrogen, and n has a value from at least 1 to about 200; each $R^2$ individually is chosen from the group consisting of R and $R^1$; x has a value from about 5 to about 400; and y has a value of at least 1 except that when $R^2$ is $R^1$, y may be zero, and (d) an organic oil-in-water type surfactant having an HLB value of from 8 to 18 inclusive, which may or may not be present.

* * * * *